United States Patent [19]

Bush et al.

[11] Patent Number: 5,683,447
[45] Date of Patent: *Nov. 4, 1997

[54] LEAD WITH SEPTAL DEFIBRILLATION AND PACING ELECTRODES

[75] Inventors: M. Elizabeth Bush, Fremont; Eric S. Fain, Menlo Park; Drew A. Hoffmann, Los Gatos; Benjamin D. Pless, Atherton, all of Calif.

[73] Assignee: Ventritex, Inc., Sunnyvale, Calif.

[*] Notice: The term of this patent shall not extend beyond the expiration date of Pat. No. 5,476,500.

[21] Appl. No.: 574,802

[22] Filed: Dec. 19, 1995

[51] Int. Cl.⁶ .................................................. A61N 1/05
[52] U.S. Cl. .................................................. 607/126
[58] Field of Search ........................... 607/116, 119, 607/122, 126, 127, 128, 130, 131; 128/642

[56] References Cited

U.S. PATENT DOCUMENTS

| | | |
|---|---|---|
| 3,902,501 | 9/1975 | Citron et al. |
| 4,233,992 | 11/1980 | Bisping. |
| 4,354,497 | 10/1982 | Kahn. |
| 4,402,329 | 9/1983 | Williams. |
| 4,458,677 | 7/1984 | McCorkle, Jr. |
| 4,577,634 | 3/1986 | Gessman. |
| 4,677,990 | 7/1987 | Neubauer. |
| 4,790,317 | 12/1988 | Davies. |
| 4,799,493 | 1/1989 | DeFault ................... 128/705 |
| 4,827,940 | 5/1989 | Mayer et al. ............ 128/642 |
| 4,858,623 | 8/1989 | Bradshaw et al. |
| 5,010,894 | 4/1991 | Edhag. |
| 5,044,375 | 9/1991 | Bach, Jr. et al. |
| 5,050,601 | 9/1991 | Kupersmith et al. |
| 5,174,289 | 12/1992 | Cohen. |
| 5,267,560 | 12/1993 | Cohen .................... 607/25 |
| 5,314,962 | 5/1994 | Heil, Jr. et al. ......... 607/128 |
| 5,374,287 | 12/1994 | Rubin ..................... 607/131 |
| 5,439,485 | 8/1995 | Mar et al. .............. 607/119 |
| 5,443,492 | 8/1995 | Stokes et al. .......... 607/131 |
| 5,456,706 | 10/1995 | Pless et al. ............ 607/122 |
| 5,476,500 | 12/1995 | Fain et al. ............. 607/126 |

OTHER PUBLICATIONS

"Alternative Lead Positioning in the Right Ventricular Outflow Tract in Transvenous Implantation of ICDs" Wolfhard, et al., *PACE*, vol. 18, Jan. 1995, Part II, pp. 179–181.

"Ventricular Pacing Site Does Make a Difference: Improved Left Ventricular Function with Septal Pacing" Karpawich, et al., *PACE*, vol. 17, 315, Apr. 1994, Part II, p. 820.

"Septal His–Purkinje Ventricular Pacing in Canines: A New Endocardial Electrode Approach", Karpawich, et al., *PACE*, vol. 15, Nov. 1992, Part II, pp. 2011–2015.

"A New dual Chamber Signle Lead System", Hirschberg, et al., *PACE*, vol. 17, No. 1994, Part II, pp. 1870–1872.

*Primary Examiner*—William E. Kamm
*Assistant Examiner*—George R. Evanisko
*Attorney, Agent, or Firm*—Steven M. Mitchell; M. Elizabeth Bush; Mark J. Meltzer

[57] ABSTRACT

A lead system for use with an implantable pacemaker/cardioverter/defibrillator. The lead system includes a securable pace/sense electrode positioned between the distal tip of the lead and the tricuspid valve. The distal tip of the lead is positioned at the apex of the right ventricle and may or may not be secured there by a second fixation means such as a screw tip or tines. The securable pace/sense electrode allows the defibrillation electrode to be accurately positioned by the patient's surgeon and maintained in intimate contact with the septum wall of the patient's heart, thereby reducing defibrillation thresholds; it provides a sense signal from the region of the His bundle or AV node, which can be used with other electrodes to distinguish between various arrhythmias; and it provides more physiologic pacing leading to greater cardiac output.

18 Claims, 5 Drawing Sheets

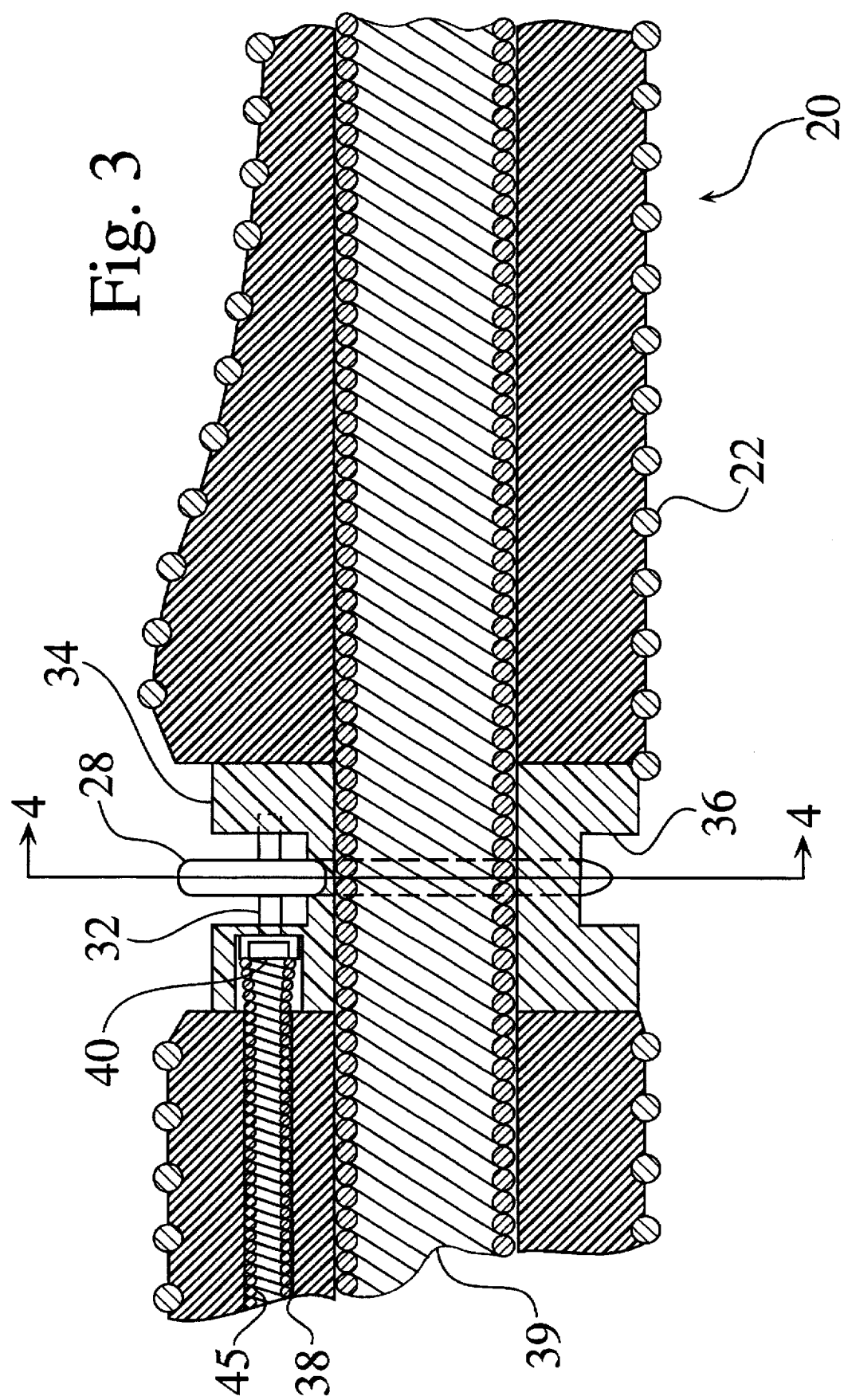

LEAD WITH SEPTAL DEFIBRILLATION AND PACING ELECTRODES

FIELD OF THE INVENTION

The present invention relates generally to lead systems for arrhythmia control devices, and more specifically to an endocardial defibrillation lead having a mechanism that can be used both for septal fixation of the defibrillation electrode and for pacing and sensing.

BACKGROUND OF THE INVENTION

The use of electrical signals to stimulate or steady heart rhythm (pacing) or to restore heart rhythm when the muscle fibers of the heart undergo very rapid irregular contractions, which result in very little pumping of blood (defibrillation), is a well accepted, lifesaving medical technique. Implantable cardioverter/defibrillator devices have been under development since at least the 1960's. The term cardioverter is used to mean a device for the correction of ventricular tachycardia (abnormally rapid heart rate of about 100-240 beats per minute) by discharging electrical energy into the heart. The term defibrillation is used to refer to high voltage shocks which terminate fibrillation (a rapid, chaotic heart rhythm resulting in no effective pumping of blood.) Implanted defibrillation is normally accomplished by passing a current between at least a pair of internally placed electrodes. The electrode arrangement may include an endocardial lead which is transvenously positioned within the heart of the patient so that one defibrillation electrode is within the right ventricle (RV). The other electrode, in the form of a flexible, substantially planar patch, is positioned outside the heart, either subcutaneously or within the thoracic cavity next to the left ventricle. Alternatively, the housing of the defibrillator may be used as an electrode. In other systems an electrode is positioned transvenously within the superior vena cava (SVC). The SVC electrode may be used in place of or in addition to the patch electrode. Electrical current is supplied to the electrodes by a battery powered pulse generator implanted under the skin of the patient, either in the abdominal or pectoral region. Improving the conductance path between the patch electrode (or device housing or SVC electrode) and the right ventricular electrode results in reduced energy required per defibrillation pulse and this may increase the lifetime of the system or allow for the use of smaller batteries.

For purposes of defibrillation, it is desirable to maximize the contact of the defibrillation electrode with the heart wall, preferably the septum between the right and left ventricles. Such intimate contact with the heart tissue makes defibrillation more effective by lowering the defibrillation threshold (DFT).

One prior art technique for positioning one or more defibrillation electrodes near the septum has used a lead system which includes a plurality of flexible electrodes which, when released, laterally expand into positions which bear resiliently against the surrounding heart walls. See U.S. Pat. No. 5,010,894 to Edhag and U.S. Pat. No. 4,998,975 to Cohen et al. These systems however, are somewhat complex and may be difficult to remove after chronic use. Additionally, the systems do not allow significant control in the placement of the electrodes.

A number of techniques have been developed for fixation of the distal end of transvenous endocardial leads within the heart of a patient. One such endocardial electrode is described in U.S. Pat. No. 3,902,501 to Citron et al. which uses a plurality of pliant fixation tines which extend at an acute angle to the lead body from the distal tip of the lead. When the lead is extended into the right ventricle, the tines act as an anchor catching in the trabeculae of the heart wall. Over time, the growth of tissue around the tines will further act to secure the lead tip in place. Another common prior art technique for lead fixation uses a helical or "screw" tip fixation device which extends from the distal tip of the lead body. A stylet or other mechanical means extending through the lead body is used to rotate the screw tip to cause it to bore into the heart tissue. Another fixation technique for a pacemaker lead is disclosed in U.S. Pat. No. 4,858,623 to Bradshaw et al. A rigid hook for engaging tissue is pivotally fastened to the lead in the vicinity of the electrode. The tip of the hook is normally resiliently urged into a recess in the lead adjacent to the electrode. A mechanism is coupled to the lead to permit the normal bias on the hook tip to be overcome to cause the hook to extend outward from the electrode. Each of these techniques is used to affix the distal tip of the lead body to the tissue of a patient's heart. However, with each of these prior art techniques, the positioning of the lead body is not accurately controlled, if at all.

Many of the prior art fixation techniques have been developed for use with pacemaker leads. With standard pacemaker leads, positioning of the distal tip of the lead is all that is required since the lead body is simply an insulated connector. Endocardial defibrillation leads, however, include a defibrillation electrode which extends along the lead body. Typically, the defibrillation electrode of such prior art leads is fixated chronically by fibrosis or not at all and its placement is not accurately controlled at the time of implant.

Additionally, most RV defibrillation leads also include a pacing electrode at the distal tip. In most patients, the lead is generally positioned with the pacing electrode as close to the RV apex as possible, resulting in pacing pulses delivered to the apex. Recent literature shows that hemodynamics could be improved by pacing from the intraventricular septum instead of the RV apex. See for example Karpawich et al., "Septal His-Purkinje Ventricular Pacing in Canines: A New Endocardial Electrode Approach," PACE 1992; 15:2011 and "Ventricular Pacing Site Does Make a Difference: Improved Left Ventricular Function with Septal Pacing," PACE 1994; 17: 820.

It is a first object of the invention to provide a transvenous defibrillation lead for use with an implantable cardioverter/defibrillator which allows precise defibrillation electrode placement in intimate contact with the intraventricular septum.

It is a second objective of the invention to provide a defibrillation lead having a pacing electrode that delivers pacing pulses to the septum.

It is a third objective to meet the first two objectives without unnecessarily complicating the lead structure, thereby maintaining small size and good reliability.

It is a fourth objective to provide a defibrillation lead having two ventricular sensing sites for tachyarrhythmia discrimination.

SUMMARY OF THE INVENTION

The present invention provides a novel transvenous lead system which allows precise placement and maintenance of the defibrillation electrode and pacing electrode along the intraventricular septum. This is accomplished by providing a securable septal pacing electrode spaced along the length of the lead body for securing the defibrillation electrode to the septum between the fight and left ventricle. The lead system includes a lead body with a proximal end for connection to an implantable cardioverter/defibrillator and a distal end for transvenous insertion into the right ventricle of a patient's heart. As with most standard RV defibrillation leads, the distal tip of the lead is typically positioned in the apex of the right ventricle, and may include fixation means such as a screw tip or tines. A defibrillation electrode begins near the distal tip and rims back along the length of the lead body. A securable septal pacing electrode is spaced along this portion of the lead body between the apex and the tricuspid valve. In addition to pacing, the "securable septal pacing electrode" may also be used for sensing. In one embodiment, the securable septal pacing electrode comprises a hook which is rotated out from the lead body for deployment and then counter rotated to pierce myocardial tissue and cause the lead body to be secured against the septum. The hook is initially in a retracted position within a recess in the lead body to provide ease of insertion of the lead body through a vein into the heart. The hook may have either a circular or elliptical or other appropriate cross section. This embodiment facilitates explant of the lead system since the hook may be rotated out of the septum and then back into the recess for removal. The lead body includes a septal pacing conductor which extends along a portion of the lead body parallel to the central lumen of the lead. A fixation stylet may be inserted through the lumen of the septal pacing conductor during implant and used to rotate the hook first away from the lead body and then into the heart tissue.

In an alternative embodiment of the invention, a guiding catheter is used for placement of the lead, thereby shielding venous tissue from potential damage caused by the securable septal pacing electrode during implant. This shielding may alternatively be accomplished by encapsulating the septal pacing electrode in a material such as mannitol which harmlessly dissolves following exposure to body fluids.

BRIEF DESCRIPTION OF THE DRAWINGS

The various features and advantages of the present invention may be more readily understood with reference to the following detailed description taken in conjunction with the accompanying drawings in which:

FIG. 3 shows a cross-sectional view of a portion of the lead shown in FIG. 1;

DETAILED DESCRIPTION OF THE INVENTION

Figure 1:
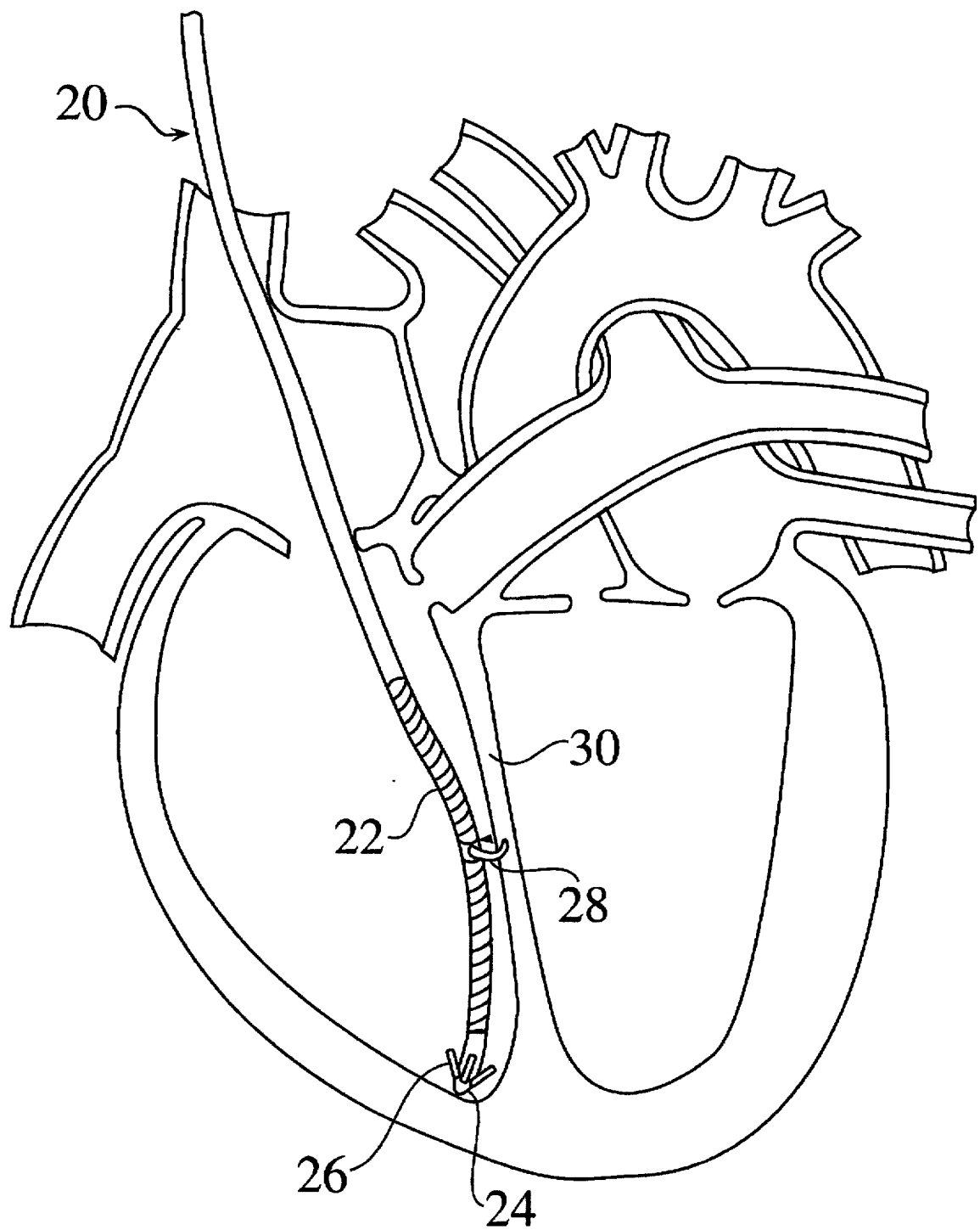
FIG. 1 shows a sectional view of a heart having a transvenous lead according to the invention inserted therein.

An endocardial lead system according to the invention will now be described with reference to FIGS. 1-6. An endocardial lead 20 shown in FIG. 1 includes a defibrillation electrode 22 proximal of the distal end of the lead and extending along the lead body, and a pacing/sensing electrode 28 positioned in the region of the defibrillation electrode and secured to the patient's intraventricular septum. The proximal end of lead 20 is connected to an implanted cardioverter/defibrillator (not shown) of known construction. The distal tip may include a pacing/sensing tip electrode 24, and tines 26 to aid in fixation of the distal end within the apex of the patient's heart. In an alternative equally preferred embodiment, the distal fixation device may include a helical screw tip, which may or may not be electrically active for pacing/sensing. In another alternative embodiment, the tip may include no fixation device and/or no distal pacing tip electrode at all. Without a distal fixation device, the distal tip is retained in the apex region of the right ventricle by fixation of the lead body in the vicinity of the defibrillation electrode 22 to the ventricular septum wall 30 as described below with respect to FIGS. 2–5. Defibrillation electrode 22 of lead 20 may be used in conjunction with a subcutaneous (SQ) patch electrode or defibrillator housing electrode (not shown) for defibrillation. In addition to or instead of the SQ electrode, a superior vena cava (SVC) electrode may be used, and may be located on lead 20 or may be on a separate lead. Septal pacing electrode 28 may be used to pace the ventricles as needed, and will provide improved hemodynamics as compared with the typical method of pacing at the apex from a tip electrode such as electrode 24. Either electrodes 28 and 22 (or SQ), or electrodes 24 and 22 (or SQ), may be paired for sensing. As another alternative, both pairs may be used to discriminate between various arrhythmias, using the techniques of one or more of the following U.S. Patents, which are incorporated herein by reference in their entirety: 4,354,497 to Kahn; 4,790,317 to Davies; and 4,799,493 to DuFault.

Figure 2:
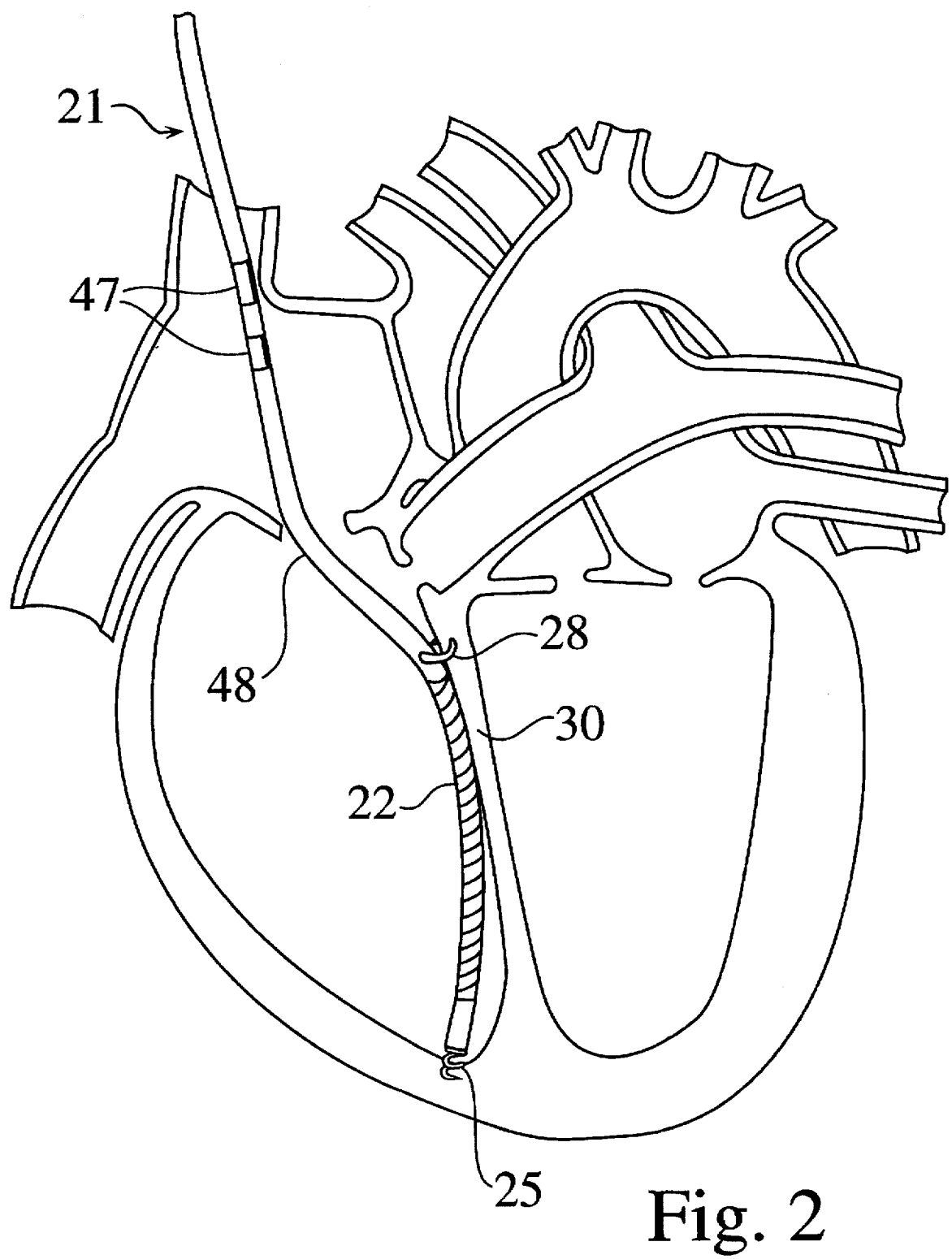
FIG. 2 shows a sectional view of a heart having an alternative embodiment of a transvenous lead according to the invention inserted therein.

FIG. 2 shows an endocardial lead 21 having a defibrillation electrode 22 proximal of the distal end of the lead and extending along the lead body, and a pacing/sensing electrode 28 positioned just proximal of defibrillation electrode 22 and secured to the patient's intraventricular septum. The lead body has a curve 48 imparted to it to aid in positioning defibrillation electrode 22 against septum 30. During implant, the lead is stiffened with a stylet, straightening curve 48 for insertion through an introducer sheath and through a vein. Upon removal of the stylet, or insertion or a less stiff stylet, the lead body resumes its curved shape to guide defibrillation electrode 22 and septal pacing electrode 28 toward septum 30. The distal tip is shown with a helical screw tip 25, which may be electrically active for pacing/sensing, may be active for defibrillation, such as described in U.S. Pat. No. 5,374,287 to Rubin, or may be electrically inactive.

It should be noted that the steps of positioning the distal tip in the apex, positioning the defibrillation electrode against the septum, securing the distal tip to the apex, and securing the septal pacing electrode to the septum can occur in various orders. The most options in step order are available if both pacing electrodes are extendable and retractable and do not require rotation of the entire lead to engage the tissue.

Septal pacing electrode 28 may be used to pace the ventricles as needed, and will provide improved hemodynamics as compared with the typical method of pacing at the apex from a tip electrode such as electrode 24. Either electrodes 28 and 22 or electrodes 25 and 22 may be paired for sensing. As another alternative, both pairs may be used to discriminate between various arrhythmias, using the techniques as described with respect to FIG. 1 above.

Also included on lead 21 are two atrial sensing electrodes 47, preferably located 10.5 to 17 centimeters from the distal end of the lead. Sensing from the pair of atrial electrodes 47 (or from atrial electrodes on a separate lead), from electrode 28 paired with either electrode 22 or a SQ electrode (not shown), and from electrode 25 paired with either electrode 22 or a SQ electrode, may provide the necessary signals to discriminate between various arrhythmias, using the technique of the U.S. Pat. No. 4,577,634 to Gessman, which is incorporated herein by reference in it's entirety. The invention would be practiced by substituting the septal electrode 28 for Gessman's low right atrial electrode.

FIG. 3 shows a portion of the lead 20 in cross-section which includes the defibrillation electrode 22 in the form of a conductive coil wound around the periphery of the lead body. The coil may be of the type assigned in U.S. Pat. No. 5,439,485, which is assigned to the assignee of the present application and is incorporated herein by reference. Other known electrode configurations may also be used. Coil 22 is connected to a lead conductor (not shown) at at least one point, preferably its distal end. A pacing hook 28 is positioned in the region of the defibrillation electrode, preferably four to ten centimeters from the distal end of the lead. Pacing hook 28 may have various cross sectional geometries including circular to provide a cylindrical hook body and rectangular to provide a flat, ribbon body. In either case, the hook is tapered to a sharp point at its tip. The ribbon configuration provides flexibility along the longitudinal extent of the lead and rigidity in the transverse plane. Pacing hook 28 pivots on a pin 32 which is mounted in a fixation ring 34 within a recess 36. Pacing hook 28 is typically a biocompatible metal such as platinum/iridium. Fixation ring 34 is preferably non-conductive, such as ceramic, acetal, or parylene coated MP35N. A septal pacing conductor 45 extends through lumen 38, which lies along lead 20 parallel to and spaced from a lead central lumen 39. The proximal end of septal pacing conductor 45 is electrically coupled to a lead connector (not shown) for connection to a pulse generator. The distal end of conductor 45 is electrically coupled to pin 32, which is in turn electrically coupled to pacing hook 28. Lumen 38 may have a seal at its distal end to prevent intrusion of body fluids. Central lumen 39 is shown including apical pacing conductor coil 41 which is electrically coupled to apical pacing electrode 24 (shown in FIG. 1).

Figure 4A:
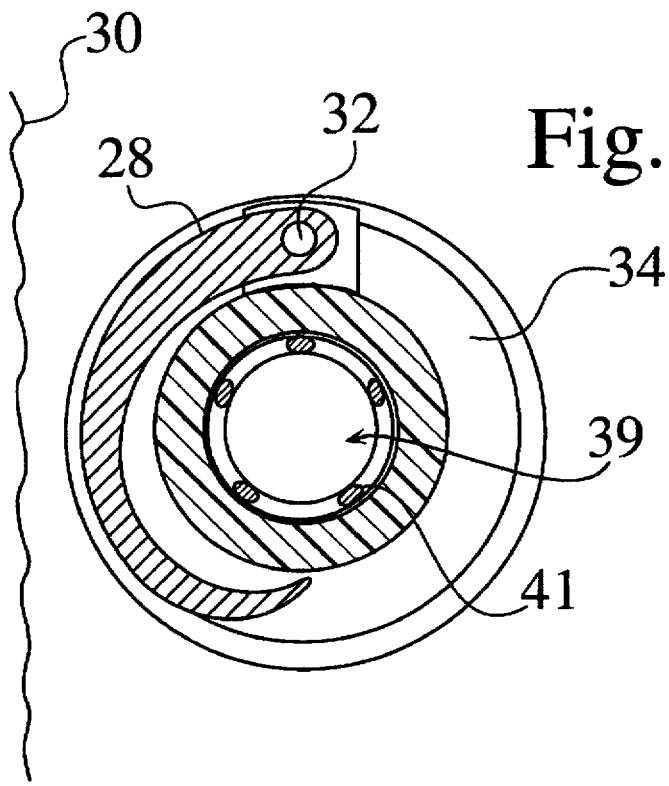
FIG. 4A shows a cross-sectional view of the lead of the invention along section 4—4 of FIG. 3.
Figure 4B:
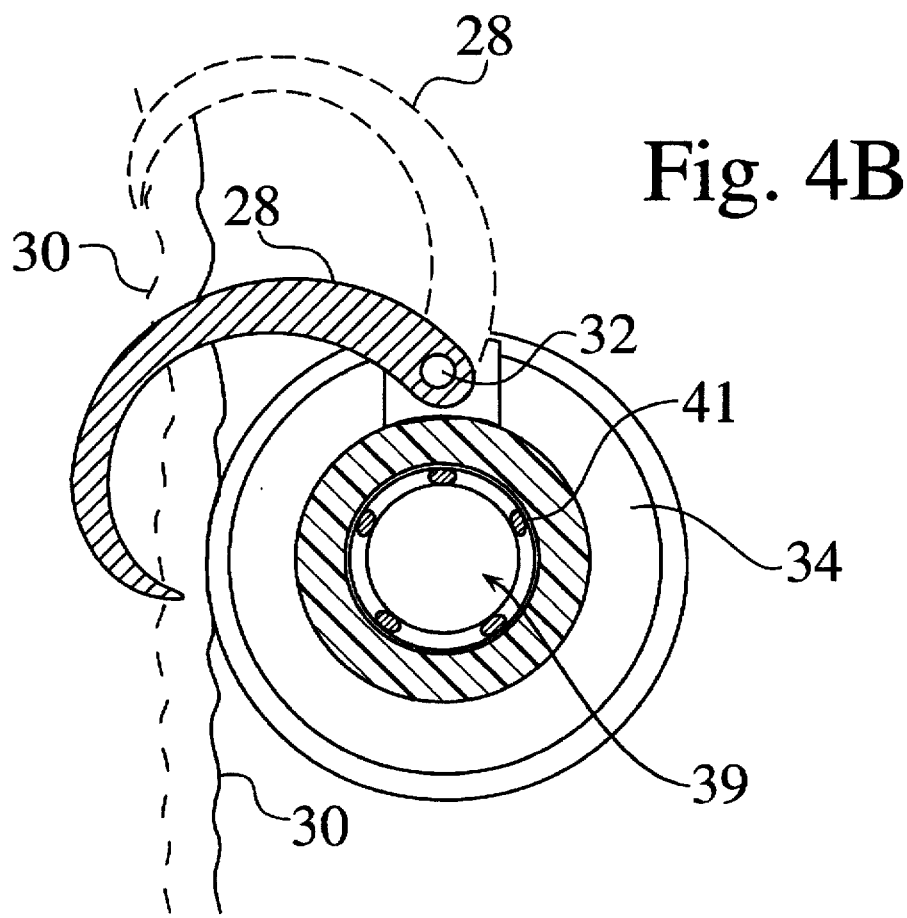
FIG. 4B shows the cross-section of FIG. 4A with the hook deployed in the septum.

During implantation of the lead, hook 28 is retracted within recess 36 which extends around the periphery of fixation ring 34 as shown in FIGS. 3 and 4A. Once the distal end of lead 20 has been positioned within the right ventricle with the defibrillation electrode 22 proximate the septum 30, hook 28 is deployed by rotating it away from the lead body. This is accomplished using a fixation stylet which is inserted through lumen 38. The stylet has a slot head at its distal end which interfaces with a slot 40 in the head of pin 32. Alternatively, conductor 45 may be stiff enough to transmit torque to pin 32 without insertion of a stylet; this stiffness may be imparted to conductor 45 by filling it or binding it with polyurethane or a polytetrafluoroethylene or the like. After the hook 28 is deployed away from fixation ring 34, it may be rotated in the opposite direction to pierce the myocardial tissue of the septum 30 to securely fix the defibrillation electrode 22 against the septum as shown in FIG. 4B. A depth of about one to three millimeters is sufficient to ensure fixation without any significant damage to the heart tissue. Attachment in this manner allows for later removal in the event this is so desired. The implanting surgeon will position the lead and actuate the fixation mechanism prior to tunneling the remainder of the lead to the pulse generator implanted in either the abdominal or pectoral region.

In some embodiments of the invention, the hook may extend out from the lead body during implantation. In this case, as described above, the hook is flexible in the direction of the lead axis and is stiff in the transverse plane. This reduces the potential for damage of the blood vessels or heart valve during an implant or explant surgical procedure. Additionally, the lead can be rotated or "sptm" in the reverse direction of the hook by the surgeon as the lead is being inserted to prevent the hook from catching on tissue. In such embodiment, the hook may be covered with a biocompatible material which is soluble in body fluids in a manner such as is described in U.S. Pat. No. 4,827,940 to Mayer et al., which patent is incorporated herein by reference. Mannitol or other sugars may be used. In this manner, the hook has a smooth coating during insertion of the lead thereby protecting the vein through which the lead is deployed. During and following insertion of the lead, the coating begins to dissolve and expose the hook for the fixation step. Alternatively, the fixation mechanism may be shielded during the implantation procedure by using an insertion catheter in a known manner.

Figure 5:
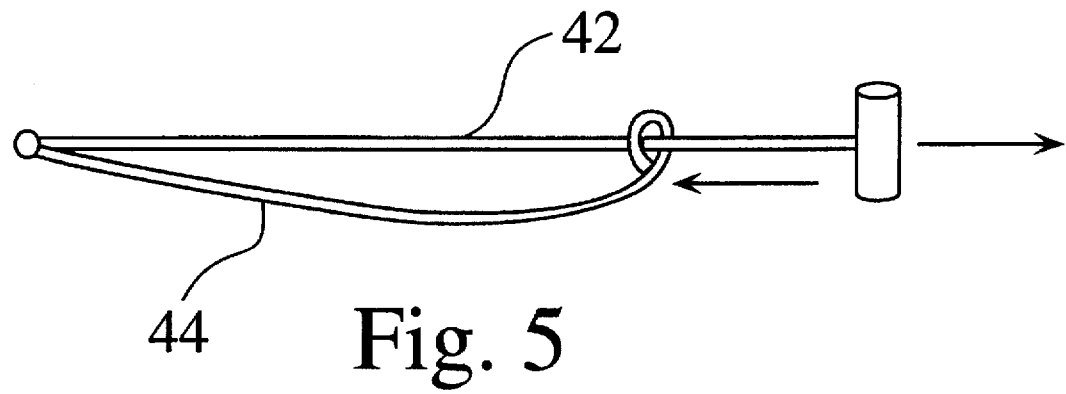
FIG. 5 is a diagrammatic representation of a bowing stylet used in positioning the lead of the invention.

FIG. 5 is a diagrammatic representation of a double, bowing stylet which may be used to flex the electrode against the septum. Pulling on one arm 42 of the stylet and pushing on the other arm 44 causes the pair to bow a sufficient amount to position the defibrillation electrode. Use of this technique for steerable guide wires is known in the art. Alternatively, a stylet may be shaped with an appropriate curvature or bend and then inserted into the central lumen of the lead body to position the fixation mechanism against the septum. Another technique for achieving the desired lead curvature is disclosed in U.S. Pat. No. 4,677,990 to Neubauer, which patent is incorporated herein by reference. A thread is anchored distally of the area of curvature and extends within the central lumen to the area of curvature. There the thread exits the central lumen and extends along the inside of an outer insulating sheath. The thread then reenters the central lumen and extends to the proximal end. By pulling on the thread, the lead is caused to curve in the area where the thread runs outside the central lumen.

In another alternative embodiment of the invention, a fixation device such as the one disclosed in U.S. Pat. No. 4,233,992 to Bisping, which patent is incorporated herein by reference, may be used to secure the defibrillation electrode to the septum. The fixation mechanism includes a spiral-shaped sharp fixing hook which may be provided with a spring winding. The hook is released once the lead body is in place and the spring action causes the hook to pierce the septum and fix the electrode thereto. As an alternative to using a spring to actuate the fixation hook, a stylet may be used to torque the spiral and "screw" it into the septum.

Figure 6:
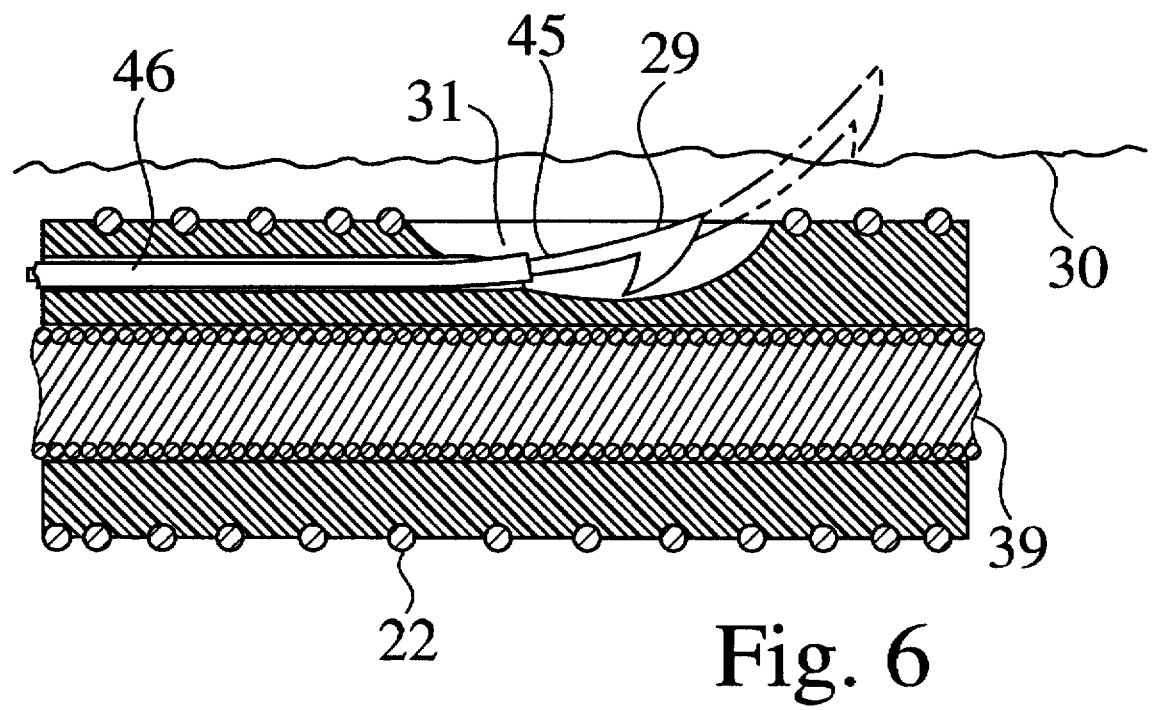
FIG. 6 is a cross-sectional view of a septal pacing electrode of an alternative embodiment of the invention.

Another alternative embodiment of the invention is illustrated in cross section in FIG. 6. Instead of the pivoting pacing hook 28 shown in FIG. 3, which is not movable in the axial direction with respect to the lead body, FIG. 6 shows a septal pacing electrode 29 that is axially movable. In FIG. 6, electrode 29 is shown as a barb; it may alternatively be a rotatable hook or helix which may be extended and retracted. As shown in FIG. 6, extendable/retractable pacing barb (or hook or helix) electrode 29 is positioned in a recess 31 during implantation. Once defibrillation electrode 22 is positioned against septum 30, pacing electrode 29 is pushed out of recess 31 and pierces septum 30. A conductor 45 is electrically coupled to electrode 29 and may be used to push it out of recess 31; alternatively, a stylet (not shown) through conductor 45 may be used to extend electrode 29 (and to rotate electrode 29 in the case of a hook or helix). Conductor 45 may be insulated with a material 46 such as parylene, polyimide, or polytetrafluoroethylene. A double bowing stylet may be used to assist in positioning the defibrillation electrode 22 against the septum. Additionally, an insertion catheter or soluble coating may be used to shield the fixation mechanism during implantation as described above.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. An endocardial defibrillation lead comprising:
    a lead body having a distal end for positioning within a patient's heart and a proximal end for connection to an implantable pulse generator;
    a defibrillation electrode positioned on said lead body near said lead body distal end;
    a securable septal pacing electrode positioned on said lead body proximal of said distal end of said lead body for securing said defibrillation electrode to the intraventricular septum of said patient's heart; and
    means disposed at said distal end for securing said distal end to a separate portion of said patient's heart.

2. The endocardial defibrillation lead of claim 1 wherein said securable septal pacing electrode is positioned on said lead body four to ten centimeters from said distal end of said lead body.

3. The endocardial defibrillation lead of claim 1 wherein said securable pacing electrode is extendable and retractable.

4. The endocardial defibrillation lead of claim 1 wherein said securable pacing electrode comprises a barb.

5. The endocardial defibrillation lead of claim 1 wherein said securable pacing electrode comprises a hook.

6. The endocardial defibrillation lead of claim 1 wherein said lead body includes a lumen extending therethrough, said lead further including a stylet for positioning within said lumen and having a distal end adapted to actuate said securable electrode whereby said securable electrode is caused to extend laterally from said lead body into the intraventricular septum of said patient's heart.

7. The endocardial defibrillation lead of claim 6 wherein said lumen is spaced radially from and parallel to the central axis of said lead body.

8. The endocardial defibrillation lead of claim 1 wherein said means disposed at said distal end comprises a plurality of tines oriented at an acute angle along said lead body.

9. The endocardial defibrillation lead of claim 1 wherein said means disposed at said distal end comprises a helical screw.

10. The endocardial defibrillation lead of claim 9 wherein said helical screw is electrically connected to said defibrillation electrode.

11. The endocardial defibrillation lead of claim 1 wherein said lead body further includes a distal pacing/sensing electrode positioned at said distal end of said lead body.

12. The endocardial defibrillation lead of claim 1 wherein said lead body is curved to urge said defibrillation electrode against said patient's intraventricular septum.

13. The endocardial defibrillation lead of claim 1 wherein said defibrillation electrode has a proximal end and a distal end, and wherein said securable septal pacing electrode is located between said proximal end and said distal end of said defibrillation electrode.

14. The endocardial defibrillation lead of claim 1 wherein said defibrillation electrode has a proximal end, and wherein said securable septal pacing electrode is located proximal of said defibrillation electrode proximal end.

15. The endocardial defibrillation lead of claim 1 and further including at least one atrial sensing electrode located proximal of said securable septal pacing electrode.

16. A method for implanting the lead of claim 1, comprising the steps of:
    (a) positioning said distal end in said patient's right ventricular apex; and
    (b) securing said lead body against said patient's intraventricular septum using said securable septal pacing electrode.

17. The method of claim 16 wherein said step (b) precedes step (a).

18. The method of claim 16 and further comprising the step of:
    (c) securing said distal end to said patient's heart.

* * * * *